(12) United States Patent
Azizian et al.

(10) Patent No.: US 8,629,081 B2
(45) Date of Patent: Jan. 14, 2014

(54) TIME/TEMPERATURE INDICATORS

(75) Inventors: Farid Azizian, Bicester (GB); Michael William Leonard, Tonbridge (GB)

(73) Assignee: Sun Chemical Corporation, Parsippany, NJ (US)

( * ) Notice: Subject to any disclaimer, the term of this patent is extended or adjusted under 35 U.S.C. 154(b) by 1556 days.

(21) Appl. No.: 12/066,582

(22) PCT Filed: Sep. 14, 2006

(86) PCT No.: PCT/US2006/035679
§ 371 (c)(1),
(2), (4) Date: Jun. 30, 2008

(87) PCT Pub. No.: WO2007/035365
PCT Pub. Date: Mar. 29, 2007

(65) Prior Publication Data
US 2008/0269050 A1    Oct. 30, 2008

(51) Int. Cl.
*B41M 5/34* (2006.01)
(52) U.S. Cl.
USPC .......................... 503/206; 503/204; 503/226

(58) Field of Classification Search
CPC ...................................................... B41M 3/005
USPC ......................................... 503/204, 206, 226
See application file for complete search history.

(56) References Cited

U.S. PATENT DOCUMENTS

| 4,917,503 | A | * | 4/1990 | Bhattacharjee | 374/102 |
| 5,254,473 | A | | 10/1993 | Patel | |
| 6,544,925 | B1 | | 4/2003 | Prusik et al. | |
| 7,998,900 | B2 | * | 8/2011 | Wyres et al. | 503/201 |
| 2008/0026224 | A1 | * | 1/2008 | Blank | 428/411.1 |

* cited by examiner

*Primary Examiner* — Bruce H Hess

(57) ABSTRACT

By printing a bar code (comprising dark and light regions) or parts of such a bar code with an ink containing a dye, which changes color in the presence of an acid or a base to remove the contrast between the regions of the bar code, and a neutral compound which releases an acid or a base on exposure to energising radiation, a bar code can be produced that becomes unreadable after a pre-determined interval. This can be used as a time/temperature indicator to ensure that products, which might be perishable, associated with such a bar code are not used by the public.

24 Claims, No Drawings

TIME/TEMPERATURE INDICATORS

CROSS REFERENCE TO RELATED APPLICATIONS

This application is the United States national phase filing of the corresponding international application number PCT/US2006/035679 filed on Sep. 14, 2006, which claims priority to and benefit of the Great Britain application no. 0518948.5 filed Sep. 16, 2005, each of which is hereby incorporated herein by reference.

The present invention relates to new time/temperature bar codes based on colour changes in dyes as a result of a reaction with acids or bases generated by energising radiation.

Many packaged goods, notably foodstuffs and medicines, have a limited shelf life, and such goods commonly have a "use by" date printed on packaging associated with the goods. However, this is, at best, only a crude indication, as the rate at which such goods deteriorate is a function of the temperature at which they are kept as well as the length of time for which they are kept. Moreover, the temperature may vary considerably during the life of the goods. For example, a product may be bought from a shop, where it is kept in a refrigerator, carried through a sunny car park, where its temperature rises, stored in a car, where its temperature rises further, and finally stored in a domestic refrigerator, where its temperature is lowered, but may still go up and down as the refrigerator door is opened and closed. Alternatively, at an earlier stage in the retail chain, a consignment of products may be loaded on a pallet, stored in a cool or refrigerated environment, and then transported in a refrigerated vehicle to the shop where the products are to be sold. Estimates of the "use by" date might assume a controlled or refrigerated environment throughout this chain. However, it is possible that the pallet could be taken from its cool or refrigerated environment prior to arrival of the refrigerated vehicle and left standing in the sun, and similarly it could be taken from the vehicle and left for some time before it is transferred once again to a refrigerated environment. In such a case, the "use by" date seen by the ultimate purchaser could be wildly optimistic, and the purchaser could have bought goods which are already in a dangerous or unpalatable state. Moreover, it is a requirement in many states that perishable foods should be traceable through the supply chain in such a way that the point of non-compliance with storage requirements can be identified.

It would, therefore, be desirable to provide an indicator on packaging associated with the goods which will react to changing temperatures over time in the same way as do the goods themselves. These are referred to as "time/temperature indicators". A number of proposals have been made for such time/temperature indicators. For example, 3M's Monitor-Mark (trade mark) uses the principle of diffusion along a wick to provide a time/temperature indicator. VITSAB's Time/Temperature Indicator is based on the colour change caused by the controlled enzymatic hydrolysis of a lipid substrate. Lifelines Inc.'s FreshCheck (trade mark) is based on a polymerisation reaction leading to a coloured polymer, and is suggested for use, inter alia, with foodstuffs.

Although all of these are successful in their fields, they are all relatively expensive and add significantly to the cost of the products to which they are applied. They cannot, therefore, be used in practice with lost cost, low margin items, particularly everyday foodstuffs. Moreover, they cannot, in general, be used to identify the point of non-compliance with storage requirements.

To meet this requirement, it would be desirable to provide a time/temperature indicator that makes use of relatively cheap components and which can be applied easily, for example by printing at the time that the packaging is printed. Moreover, if the time/temperature indicator is applied to the packaging before the perishable product is packed in it, it is desirable that the indicator should be inactive until a time close to the time of packaging and then should be activated so that its response closely parallels that of the perishable product.

However, even this may not be adequate. Many shoppers, in a hurry, would simply pick up the desired goods without checking the time/temperature indicator. We have now discovered how the bar code, which, at present, is applied to virtually every perishable product on sale to the general public, may be used to prevent the sale of products which have exceeded a combination of time and temperature after which they are regarded as unsuitable for sale.

As is well known, a bar code is a series of dark parallel lines or bars separated by light spaces. The bar code is typically applied to packaging or in some other way associated with the material to be identified. The bars are of varying width and the arrangement of bars represents a number. The bar code is read by a bar code reader, which typically operates by recording the light reflected from the region of the bar code. Typically, infra red (IR) light, or any other suitable frequency of light, is emitted by the reader and the reflection is read, and translated into a number. This number may be used for various purposes, but is commonly used to identify the material with which the bar code is associated. If the distinction between the dark bars and the light spaces is not sufficient, the bar code cannot be read. We have now discovered that time/temperature indicator technology can be used to render the bar code unreadable, in a controlled manner, so that it will become unreadable at about the same time as the material it is associated with becomes dangerous or unpalatable.

U.S. Pat. No. 6,544,925 B1 discloses an activatable time-temperature indicator system, which comprises a first element consisting of a co-reactant for a colour forming reaction and a second, activator element that is affixed to the first element to activate the system. The activator element is applied separately from the first element at the time of point-of-sale label marking, whereas in the present invention, the time/temperature indicator system can be applied easily and cheaply in a single step as part of printing of the packaging.

U.S. Pat. No. 4,917,503 discloses a time/temperature indicator which comprises a thermally inactive compound comprising a leuco base and a photosensitive compound that, on exposure to actinic radiation (e.g. ultraviolet), forms an acid that converts the leuco base to a thermally active product. The photosensitive compounds suggested for use in this patent are limited to o-nitrobenzaldehyde and derivatives thereof and trihaloalcohols, materials which are recognised to be harmful to health and therefore unsuitable for use in foodstuffs or other perishable materials.

The present invention consists in a substrate on which is provided a bar code comprising a plurality of bars separated by spaces in a contrasting colour, characterised in that at least some of the bars or the spaces are coloured by a dye which will change colour in the presence of an acid or a base to reduce the contrast between the bars and the spaces, and a neutral compound which, on exposure to energising radiation, forms an acid or a base to initiate a colour change in the dye.

Note that, for the purposes of this specification, black and white are regarded as colours.

Currently, in most bar codes, the bars (generally, and preferably, although not necessarily, printed in black) are of varying widths and these different widths generate the code. Often the spaces between (generally, and preferably, although not necessarily, coloured white or a very light non-white colour) are also of varying widths. It would also be possible for the bars to be of varying widths, with the spaces of substantially equal widths, or for the bars to be of substantially equal widths and the spaces to be of varying widths.

It is preferred that all or a majority of the bars or all or a majority of the spaces are coloured by the dye which will change colour in the presence of an acid or a base. Where the bars are coloured by that dye, it is not necessary and is not preferred that the spaces should also be coloured. Most preferably, all of the bars or all of the spaces, but not both, are so coloured.

Because the acid or base is not released until the material is exposed to the energising radiation, the material may be kept for as long as necessary without affecting the bar code. However, upon exposure to the energising radiation, acid or base is released and the colour change begins. By careful selection of the energising radiation, the dye, the neutral compound and other components of the packaging material, it is possible to achieve a material where the bar code will become unreadable to a normal bar code reader at about the same time as, and ideally, slightly before, the packaged material becomes unusable.

It should be noted that the colour change should be such as to render the bar code unreadable to a standard bar code reader. The reader used in the research leading to the present invention was purchased about 4-5 years ago from Symbol Technology, inc, Bohemia N.Y., USA, Model no. LS1006-1010. Accordingly, when we refer to the bar code becoming unreadable, it is preferably unreadable to this model or a model having equivalent sensitivity—it would then, of course, be unreadable to all or most other bar code readers. A "8300L series portable terminal" using a visible laser diode and supplied by Electronic Reading Systems Ltd (ERS) was also used, with essentially the same results.

The neutral compound and the dye may be employed in the form of a simple mixture, optionally in association with binders and other conventional ingredients. Alternatively, in one preferred embodiment of the present invention, the dye and the neutral compound are present in separate layers, a first layer containing the dye and a second layer containing the neutral compound, one overlying the other, so that, upon exposure to the energising radiation, the acid or base thereby released migrates, at a rate that can be predicted, into the layer containing the dye. The rate of the reaction converting the dye to a different, and generally but not necessarily darker, colour is known and can, by suitable choice of reagents etc., be selected to approximate the rate at which the material to be associated with the bar code becomes unusable.

If desired, the first and second layers may be in direct contact with each other. Alternatively, there may be another layer or layers between them, provided that those layer(s) do not form a barrier to the migration of the acidic or basic entity.

The order of the layers may have an influence on the rate of colour change and may be chosen as desired, provided that the first and second layers are not separated by anything which would form a barrier to the migration of the acidic or basic entity. Thus, if desired, the first layer may be between the substrate and the second layer. Alternatively, the second layer may be between the substrate and the first layer.

The natures of the dyes and neutral compounds employed are, of course, inter-related. For example, in one embodiment of the present invention, the dye changes colour in the presence of an acid, for example a leuco dye or a vat dye in its non-activated (reduced) state, in which case the neutral compound is a compound which forms an acid on exposure to energising radiation, preferably a cationic photoinitiator.

The term "cationic photoinitiator" as used herein means a compound which, upon exposure to incident radiation, such as ultraviolet, forms a cation capable of initiating the polymerisation of an epoxide monomer. It will, of course, be understood that no such polymerisation is necessarily envisaged in the present invention.

In another embodiment of the present invention, the dye changes colour in the presence of a base, for example a leuco dye or a vat dye in its activated (oxidised) state, and the neutral compound in the other layer is a photolatent base. A photolatent base is a compound which, upon exposure to incident radiation, such as ultraviolet, generates a base.

Where the dye and neutral compound are in separate layers, still further alternatives are possible. For example, in a further embodiment of the present invention, one layer comprises a dye which changes colour in the presence of a base, for example a leuco dye or a vat dye in its activated (oxidised) state, and a photolatent base. The other layer contains the neutral compound, which, in this case, is a cationic photoinitiator.

In a still further embodiment of the present invention, one layer comprises a dye which changes colour in the presence of an acid, for example a leuco dye or a vat dye in its non-activated (reduced) state, and a cationic photoinitiator. The other layer contains the neutral compound, which, in this case, is a photolatent base.

In the last two embodiments referred to above, upon exposure to, for example, UV radiation, the dye in the one layer changes colour as a result of the generation of a base (if that layer also contains a photolatent base) or an acid (if that layer also contains a cationic photoinitiator). However, simultaneously, the cationic photoinitiator or photolatent base in the other layer generates an acid or a base, respectively, and this subsequently converts the dye to its other state, thus again changing its colour, but not necessarily into the same colour as its original state.

Where the present invention uses a cationic photoinitiator, there is no particular restriction on the particular compound used, and any cationic photoinitiator known in the art may be employed. Examples of such cationic photoinitiators include sulphonium salts (such as the mixture of compounds available under the trade name UVI6992 from Dow Chemical), thianthrenium salts (such as Esacure 1187 available from Lamberti), iodonium salts (such as IGM 440 from IGM) and phenacyl sulphonium salts. However, particularly preferred cationic photoinitiators are the thioxanthonium salts, such as those described in WO 03/072567 A1, WO 03/072568 A1, and WO 2004/055000 A1, the disclosures of which are incorporated herein by reference.

Particularly preferred thioxanthonium salts are those of formulae (I) and (II):

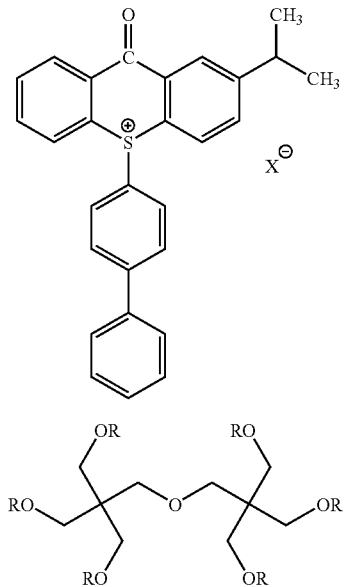

(I)

in which each R represents a group of formula (III):

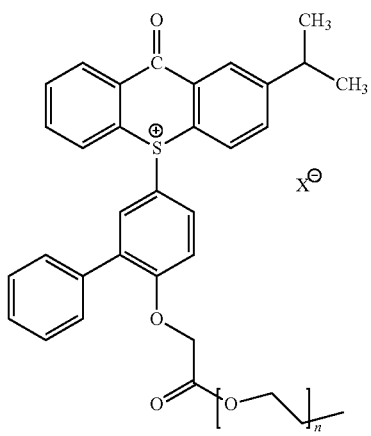

(III)

where n is a number and X⁻ is an anion, especially the hexafluorophosphates, which are available from Robinson Brothers Ltd. under the trade marks "Omnicat 550" and "Omnicat 650", respectively.

A photolatent base (sometimes called a "photobase generator") is a compound which, in its normal state, is essentially neutral, but which, upon irradiation with ultraviolet light, generates a basic compound. In general, these include classes of compounds such as carbamates, O-acyloximes, O-carbamoyloximes, formamide, amineimide and onium salts. Specific examples of such photolatent bases include:

Quaternary ammonium salts, such as 1-phenacyl-(1-azonia-4-azabicyclo[2,2,2]-octane)bromide; 1,4-dimethyl-1-phenacyl-(1-azonia-4-azabicyclohexane) bromide; and 1-naphthoylmethyl-1-phenacyl-(1-azonia-4-azabicyclo[2,2,2]octane)bromide;

Carbamates, such as 1-phenacyl-(1-azonia-4-azabicyclo[2,2,2]octane)-N,N-dimethylthiocarbamate; 1-methyl-1-phenacyl-(1-azoniacyclohexane)-N,N-dimethyldithiocarbamate; 1,4-dimethyl-1-phenacyl-(1-azoniacyclohexane)-N,N-dimethyldithiocarbamate; and 1-naphthoylmethyl-(1-azonia-4-azabicyclo[2,2,2]octane-N,N-dimethyldithiocarbamate;

Amineimides, such as 1,1-dimethyl-1-(2-hydroxy-3-phenoxypropyl)amine-p-nitrobenzimide, 1,1-dimethyl-1-(2-hydroxy-3-phenoxypropyl)amine-p-cyanobenzimide; and 1,1-dimethyl-1-(2-hydroxy-3-phenoxypropyl)amine benzimide.

N-substituted 4-(o-nitrophenyl)dihydropyridines, optionally substituted with allyl ether and/or alkyl ester groups, such as N-methyl nifedipine (Macromolecules 1998, 31, 4798), N-butyl nifedipine, N-butyl 2,6-dimethyl-4-(2-nitrophenyl) 1,4-dihydropyridine 3,5-dicarboxylic acid diethyl ester, and N-methyl 2,6-dimethyl 4-(4,5-dimethoxy-2-nitrophenyl)-1, 4-dihydropyridine 3,5-dicarboxylic acid diethyl ester;

Quaternary organo-boron photoinitiators such as those disclosed in GB-A-2 307 473, the disclosure of which is incorporated herein by reference;

α-Aminoacetophenones, such as 4-(methylthiobenzoyl)-1-methyl-1-morpholinoethane (IrgacureR 907 ex Ciba Specialty Chemicals) and (4-morpholinobenzoyl)-1-benzyl-1-dimethylaminopropane (IrgacureR 369 ex Ciba Specialty Chemicals); and The α-ammonium ketones, iminium ketones or amidinium ketones in the form of their tetraaryl- or triarylalkylborate salts as disclosed in U.S. Pat. No. 6,551,761 B1, the disclosure of which is incorporated herein by reference.

Preferred photolatent bases are the quaternary ammonium salts, carbamates, O-acyloximes, O-carbamoyloximes, formamides, amineimides and onium salts. The most preferred are 4-methoxybenzyloxycarbonyl azide, 1-benzylimidazole, benzyl-4-oxo-1-piperidinecarboxylate, fluorenylmethoxycarbonyl-4-piperidone, N-(benzyloxycarbonyl)glycinamide, N-(benzyloxycarbonyl)-1-H-pyrazole-1-carboxamidine, or N-(benzyloxycarbonyl)-2-aminoacetonitrile.

Preferably, the dye is one which can be bleached by an acid or a base. However, it is also possible to use a dye which simply changes from one colour to another in the presence of an acid or a base. One preferred class of dyes which may be used in the present invention is the class of leuco dyes, which are used in their activated state if they are to be contacted with a base, or in their inactivated state, if they are to be contacted with an acid. Leuco dyes are generally synthetic organic colourless powders which, upon oxidation/acidification (collectively referred to herein as "activation") become coloured. More details of such dyes may be found in "Chemistry and Applications of Leuco Dyes", edited by R Muthyala, published in 1997 by Plenum Publishing Corporation, the disclosure of which is incorporated herein by reference.

Examples of leuco dyes which may be used in the present invention include the known leuco dyes such as triphenylmethane compounds, fluoran compounds, phenothiazine compounds, auramine compounds, spiropyran compounds, indolinophthalide and the like. These leuco dyes may be used alone or in combination. Specific examples of such leuco dyes include the following compounds:
3,3-bis(p-dimethylaminophenyl)phthalide, 3,3-bis(p-dimethylaminophenyl)-6-dimethylaminophthalide (i.e., crystal violet lactone), 3,3-bis(p-dimethylaminophenyl)-6-diethylaminophthalide, 3,3-bis(p-dimethylaminophenyl)-6-chlorophthalide, 3,3-bis(p-dibutylaminophenyl)phthalide, 3-cyclohexylamino-6-chlorofluoran, 3-dimethylamino-5,7-dimethylfluoran, 3-dimethylamino-7-chlorofluoran, 3-diethylamino-7-methylfluoran, 3-diethylamino-7,8-benzfluoran, 3-diethylamino-6-methyl-7-chlorofluoran, 3-(N-p-tolyl-N-ethylamino)-6-methyl-7-anilinofluoran, 3-pyrrolidino-6-methyl-7-anilinofluoran, 2-[N-(3-trifluoromethylphenyl)amino]-6-diethylaminofluoran, 2-[3,6-bis(diethylamino)-9-o-chloroanilino]xanthylbenzoic acid lactam, 3-diethylamino-6-methyl-7-(m-trichloromethylanilino)fluoran, 3-diethylamino-7-(o-chloroanilino)fluoran, 3-di-n-butylamino-7-(o-chloroanilino)fluoran, 3-N-methyl-N-n-amylamino-6-methyl-7-anilinofluoran, 3-N-methyl-N-cyclohexylamino-6-methyl-7-anilinofluoran, 3-diethylamino-6-methyl-7-anilinofluoran, 3-(N,N-diethylamino)-5-methyl-7-(N,N-dibenzylamino) fluoran, 24-benzoyl leuco methylene blue, 6'-chloro-8'-methoxy-benzoindolinospiropyran, 6'-bromo-3'-methoxybenzoindolinospiropyran, 3(2'-hydroxy-4'-dimethylaminophenyl)-3-(2'-methoxy-5'-chlorophenyl)phthalide, 3-(2'-hydroxy-4'-dimethylaminophenyl)-3-(2'-methoxy-5'-nitrophenyl) phthalide, 3-(2'-hydroxy-4'-diethylaminophenyl)-3-(2'-methoxy-5'-methylphenyl)phthalide, 3-(2'-methoxy-4'-dimethylaminophenyl)-3-(2'-hydroxy-C-chloro-5'-methylphenyl)phthalide, 3-(N-ethyl-N-tetrahydrofurfuryl) amino-6-methyl-7-anilinofluoran, 3-N-ethyl-N-(2-ethoxypropyl)amino-6-methyl-7-anilinofluoran, 3-N-methyl-N-isobutyl-6-methyl-7-anilinofluoran, 3-morpholino-7-(N-propyl-trifluoromethylanilino)fluoran, 3-pyrrolidino-7-m-trifluoromethylanilinofluoran, 3-diethylamino-5-chloro-7-(N-benzyl-trifluoromethylanilino)fluoran, 3-pyrrolidino-7-(di-p-chlorophenyl)methylaminofluoran, 3-diethylamino-5-chloro-7-o-phenylethylamino)fluoran, 3-(N-ethyl-p-toluidino)-7-α-phenylethylamino) fluoran, 3-diethylamino-7-(o-methoxycarbonylphenylamino)fluoran, 3-diethylamino-5-methyl-7-(α-phenylethylamino)fluoran, 3-diethylamino-7-piperidinofluoran, 2-chloro-3-(N-methyltoluidino)-7-(p-n-butylanilino)fluoran, 3-(N-methyl-N-isopropylamino)-6-methyl-7-anilinofluoran, 3-di-n-butylamino-6-methyl-7-anilinofluoran, 3,6-bis(dimethylamino)fluorenespiro(9,3')-6'-dimethylaminophthalide, 3-(N-benzyl-N-cyclohexylamino)-5,6-benzo-7-α-naphthylamino-4'-bromofluoran, 3-diethylamino-6-chloro-7-anilinofluoran, 3-diethylamino-6-methyl-7-mesidino-4',5'-benzofluoran, 3-N-methyl-N-isoproyl-6-methyl-7-anilinofluoran, 3-N-ethyl-N-isoamyl-6-methyl-7-anilinofluoran, 3-diethylamino-6-methyl-7-(2',4'-dimethylanilino)fluoran, and the like.

The more preferred leuco dyes for use in the present invention include carbazolyl blue, indolyl red, leuco crystal violet, leuco malachite green, bis(p-dimethylaminophenyl)(9-ethylcarbazol-3-yl)methane, bisarylcarbazolylmethane, 3,3-bis(1-N-octyl-2-methyl-indol-3-yl) phthalide, 3-(N,N-diethylamino)-7-(N,N-dibenzylamino)fluoran and crystal violet lactone. A single such dye, or a mixture of any two or more such dyes, may be used.

Another class of dyes which may be used are the vat dyes. Vat dyes are a class of water insoluble dyes, such as indigo and anthraquinone derivatives. These dyes in their reduced and water soluble form, reduced by a base, are colourless or different from their original colour, whilst when oxidised, which may be by an acid, they return to their original colour and their insoluble form. Examples are Vat Blue 3, Blue 5, Vat Green 1, Methylene Violet 3RAX, Light green SF Yellowish, Leuco xylene cyanole FF and Nile Blue A. Vat dyes are especially fast to light and produce brilliant colours with high light fastness.

A further class of dyes which may be used comprises pH indicators which change colour on going from a neutral or acidic environment to a basic one, or vice versa. Examples of such compounds include: methyl violet, crystal violet, ethyl violet, ethyl orange, malachite green, methyl green, cresol red, thymol blue, bromophenol blue, bromophenol red, Congo red, methyl orange, resorcin blue, alizarin red, methyl red, litmus, bromocresol purple, chlorophenol red, bromothymol blue, phenol red, neutral red, tumaric curcumin, phenolphthalein, thymophthalein, alizarin yellow R, alizarin yellow GG, Clayton yellow, methyl yellow, tropaeolin O sodium salt, bromoxylenol blue, bromochlorophenol blue, brilliant green, metanil yellow, benzyl orange, Tashiro's indicator solution, quinaldine red, tetrabromophenol blue, α-naphthyl red hydrochloride, brilliant yellow, phenol violet, thymol violet, tropaeolin, ethyl orange sodium salt, turmeric, p-xylenol blue, bromocresol green sulphone, bromophenol blue sodium salt, m-cresol purple sodium salt, m-cresolsulfonphthalein sodium salt, quercetin dihydrate, o-cresolphthalein, α-naphtholphthalein, 2-nitrophenol, 4-nitrophenol, 3-nitrophenol, p-rosolic acid, and thymolphthalein.

A single such dye, or a mixture of any two or more such dyes, may be used.

The amounts of dye and photolatent base or acid-generating cationic photoinitiator in the time/temperature indicator composition of the present invention may vary depending on the required properties. However, in general, we prefer to employ from 0.01 to 10.0% by weight, more preferably from 1.0 to 3.0% by weight, of the leuco dye and from 0.01 to 10.0% by weight, more preferably from 0.05 to 2.0% by weight, of the photolatent base or acid-generating cationic photoinitiator, based on the weight of the whole composition. However, these amounts are not critical to the invention and amounts outside these ranges may be used, if desired. In particular, for a greater intensity of coloration, higher amounts may be used.

In addition to the dye and the photolatent base or acid-generating cationic photoinitiator, the composition may contain other components to render the composition printable. Such other components may include, for example, resins, solvents and binders [such as polyvinyl butyral (PVB), nitrocellulose, polyurethanes (PU), polyesters, cellulose acetate propionate (CAP), polyacrylates, polyamides and polyvinyl alcohol].

In particular, the compositions of the present invention may contain a polymer having a sharp and predictable melting point so that it melts at a pre-determined temperature but remains solid until that temperature is reached, Such polymers are available under the trade name "Intelimer" from Landec. Intelimer polymers can abruptly change their permeability, adhesion or viscosity when heated or cooled by just a few degrees.

An advantage of the present invention is that the bar codes and the dye/neutral compound combination may be printed using many conventional printing techniques, of which the flexographic, gravure printing and inkjet techniques are preferred, inkjet printing being especially preferred. The compositions will, of course, be formulated in accordance with the specific requirements of the printing technique used, as is well known in the art.

There is no restriction on the nature of the substrate on which the composition is printed. Examples include paper, cardboard, cellophane and various plastics films. Any plastic materials commonly used in the industry, especially for food wrapping, may be used as the plastics film. Examples of such materials include synthetic and semi-synthetic organic polymers, such as cellulose acetate, cellulose acetate butyrate (CAB), cellophane, polyvinyl chloride (PVC), polyvinyl fluoride, polyvinylidene chloride (PVDC), polyethylene, polypropylene (PP), polyamides, polyesters, polyphenylene oxide, polyethylene terephthalate (PET), polybutylene terephthalate (PBT), polymethyl methacrylate, poly(methyl pentene (TPX), polyvinyl acetal, polystyrene, acrylonitrile-butadiene-styrene (ABS), acrylonitrile-styrene-acrylate (ASA), polycarbonate, polystyrene, polyether sulphone, polyether ketones, polyimides, and copolymers and/or mixtures thereof. If desired, films made from any of these polymers may be coated with coating materials well known in the art, and/or may be laminated to a film or films made of the same or different polymers. Further examples of such plastic materials may be found in standard reference texts, such as "Plastic Films", $3^{rd}$ Edition, by J. H. Briston, published by Longman Group in 1989.

The substrate may be a part of the packaging of the product destined to be protected by the bar codes of the present invention, or it may be a tag or label associated with the product to be protected.

The indicator composition may be activated by exposure to UV radiation or similar energising radiation, including electron beam. The nature and amount of radiation used is similar to that used for the photoinitiation of UV-curable printing inks and is well known to those skilled in the art.

Provided that the combination of the dye and neutral compound will, when exposed to energising radiation, obscure the bar code, there is no particular restriction on where or how it is printed or located. For example, the combination of the dye and neutral compound may be provided as a transparent layer over the whole of the bar code. Alternatively, the combination of the dye and neutral compound may be provided as a transparent layer over a part of the bar code. For example, the combination of the dye and neutral compound may be provided simply over the lighter spaces. If desired, the bar code may be printed over the combination of the dye and neutral compound.

Where the dye and neutral compound are in separate layers, further options are available. For example, the dye may be in a first layer and the neutral compound may be in a second layer, one of the first and second layers overlying the other of the first and second layers. In this case, the first and second layers are preferably in direct contact with each other, or the first layer is between the substrate and the second layer, or the second layer is between the substrate and the first layer.

As a further option, the bar code itself may be printed using an ink containing the dye/neutral compound combination of the present invention. In this case, the dye should be so chosen as to become lighter, so as to reduce the contrast between the spaces and the bars. For this purpose, we prefer that the dye should be a leuco or vat dye in the coloured form and the neutral compound should be a photolatent base, such as those exemplified above.

The invention is further illustrated by the following non-limiting Examples.

The photoinitiator used in the Examples was obtained from Robinson Brothers Ltd. under the trade mark "Omnicat 550", and has the formula:

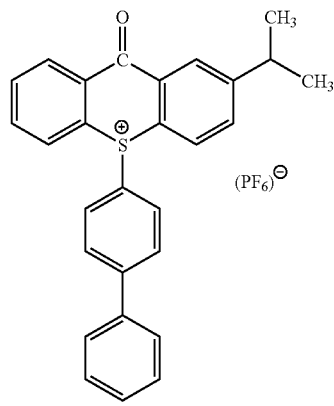

EXAMPLE 1

Development of Obscured Bar Code Reading

In order to produce a time/temperature indicator by obscuring the bar code reading, a bar code was over-printed with a solution of a formulated leuco dye and a solution of photoinitiator, using a K Printing Proofer (RK Print).

The leuco dye formulation was prepared by dissolving Pergascript Black I-2R (3-dibutylamino-6-methyl-7-anilino fluoran) (0.4 g) and Pergascript Blue S-RB (Bisarylcarbazolylmethane) (0.4 g) in 5 g of a 1:2 mixture of ethyl acetate and methyl ethyl ketone (MEK) mixture, by gentle heating and stirring with a magnetic stirrer to give a clear solution. This was then added to 20 g of a solution of CAP resin in ethyl acetate, to give coating composition (a).

The photoinitiator solution was prepared by adding a 5% solution of Omnicat in MEK (2 g) to a solution of CAP resin in ethyl acetate (5 g), to give coating composition (b).

Coating composition (a) was coated over several bar code prints and left to dry. Then coating composition (b) was coated over the first coating and air-dried. This produced a very pale green image over the bar code prints.

Coating composition (b) was coated over several bar code prints and left to dry. Then coating composition (a) was coated over the first coating and air-dried. This produced a very pale green image over the bar code prints.

The prints were irradiated with a UV dose of 0.344 mj/cm². They were then kept at different temperatures of 0° C., 27° C. and 50° C. and their progress was monitored by reading the bar code at intervals. After one week, all prints were still readable, however, the bar code prints kept at 50° C. were only read with some difficulty. After two weeks, the bar code prints kept at 27° C. and 50° C. could not be read (the bar code was obscured and not readable any longer), however, bar code prints kept at 0° C. were still readable.

EXAMPLE 2

(c) Pergascript Blue SRB solution was prepared according to Example 1(a).

(d) Photoinitiator solution was prepared according to Example 1(b).

Solutions (c) and (d) were coated on barcode prints according to Example 1.

The bar code prints were irradiated with a UV dose of 0.130 mj/cm$^2$. They were then kept at different temperatures of 0° C., 27° C. and 50° C. and their progress was monitored by reading the bar code at intervals. The results were essentially as described in Example 1.

EXAMPLE 3

(e) Pergascript Blue SRB and Pergascript Blue I-2RN solution was prepared according to Example 1(a).

(f) Photoinitiator solution was prepared according to Example 1(b).

Solutions (e) and (f) were coated on barcode prints according to Example 1.

The bar code prints were irradiated with a UV dose of 0.130 mj/cm$^2$. They were then kept at different temperatures of 0° C., 27° C. and 50° C. and their progress was monitored by reading the bar code at intervals. The results were essentially as described in Example 1.

EXAMPLE 4

Inkjet Printed Bar Codes (a) A conventional inkjet ink formulation was prepared by dissolving Brilliant Green (Basic Green 1) (0.1 g) in 3 g of isopropyl alcohol (IPA), by gentle heating and stirring with a magnetic stirrer to give a clear solution.

(b) A photolatent solution was prepared by dissolving a sample of photolatent "CG1277" (0.5 g), supplied by CIBA Speciality Chemicals, into 3 g of MEK.

(c) Solution (b) was added slowly to solution (a) while stirring, by gentle warming in a water bath.

(d) A solution of de-ionised water (40 g), butyl carbitol (2 g), surfactants (acetylenic diol type) (0.1 g) and glycol (4 g) was prepared.

(e) Solutions (c) and (d) were mixed together by gentle warming in a water bath. The resultant mixture was cooled and filtered over a 0.45 mm filter to give a clear solution and adjusted to an adequate viscosity for inkjet printing.

(f) The inkjet ink from (e) was filled into a blank HP inkjet cartridge and prepared for printing.

Several bar codes were printed for evaluation. The prints were irradiated with a UV dose of different levels. They were then kept at different temperatures of 0° C., 10° C. and room temperature (24° C.) and their progress was monitored by reading the bar code at intervals. After one week, all prints were still readable; however, the bar code prints kept at 24° C. were only read with some difficulty. After two weeks, the bar code prints kept at 24° C. and 110° C. could not be read (the colour intensity of the bar code was reduced and not readable any longer); however, bar code prints kept at 0° C. were still readable.

The invention claimed is:

1. A substrate on which is provided:
   a bar code comprising a plurality of bars separated by spaces in a contrasting color, wherein at least some of the bars or the spaces are colored by a dye which will change color in the presence of an add or a base to reduce the contrast between the bars and the spaces, and an additional layer of the dye and a neutral compound which, on exposure to energizing radiation, forms an acid or a base to initiate a color change in the dye, said additional layer provided as a transparent layer over at least a part of the bar code.

2. A substrate according to claim 1, in which said additional layer is provided as a transparent layer over the whole of the bar code.

3. A substrate according to claim 1, in which said additional layer is provided over the lighter spaces of the bar code.

4. A substrate according to cairn 1, in which the bar code is printed over said additional layer.

5. A substrate according to claim 1, wherein in said additional layer the dye is in a first layer and the neutral compound is in a second layer, one of the first and second layers overlying the other of the first and second layers.

6. A substrate according to claim 5, in which said first and second layers are in direct contact with each other.

7. A substrate according to claim 5, in which the first layer is between the substrate and the second layer.

8. A substrate according to claim 5, in which the second layer is between the substrate and the first layer.

9. A substrate according to claim 1, in which the dye is a leuco dye.

10. A time/temperature indicator comprising the substrate according to claim 9, in which said leuco dye is in its reduced form and the neutral compound is a cationic photoinitiator.

11. A time/temperature indicator according to claim 10, in which said leuco dye is carbazolyl blue, indolyl red, leuco crystal violet, leuco malachite green, bis(p-dimethylaminophen yl)(9-ethylcarbazol-3-yl)methane, bisarylcarbazolylmethane, 3,3-bis(1-N-octyl-2-methyl-indol-3-yl)phthalide, 3-(N,N-diethylamino)-7-(N,N-dibenzylamino)fluoran or crystal violet lactone.

12. A time/temperature indicator according to claim 10, in which said cationic photoinitiator is one of: a thioxanthonium salt, a sulphonium salt, a thianthrenium salt, an iodonium salt or a phenacyl sulphonium salt.

13. A time/temperature indicator according to claim 12, in which the cationic photoinitiator is a compound of formula:

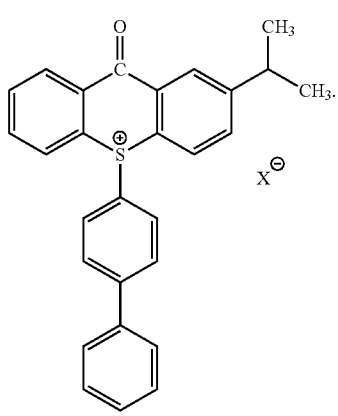

14. A time/temperature indicator according to claim 12, in which the cationic photoinitiator is a compound of formula:

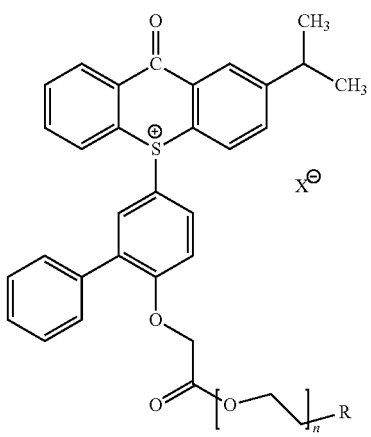

in which n is a number and R is a terminal group.

15. A time/temperature indicator comprising the substrate according to claim 1, in which said dye changes colour in the presence of a base, and the neutral compound is a photolatent base.

16. A time/temperature indicator according to claim 15, in which said dye is the activated form of carbazolyl blue, indolyl red, leuco crystal violet, leuco malachite green, bis(p-dimethylaminophenyl)(9-ethylcarbazol-3-yl)methane, bisarylcarbazolylmethane, 3,3-bis(1-N-octyl-2-methyl-indol-3-yl)phthalide, 3-(N,N-diethylamino)-7-(N,N-dibenzylamino)fluoran or crystal violet lactone.

17. A time/temperature indicator according to claim 15, in which the photolatent base is a quaternary ammonium salt, a carbamate, an O-acyloxime, an O-carbamoyloxime, a formamide, an amineimide or an onium salt.

18. A time/temperature indicator according to claim 15, in which the photolatent base is 4-methoxybenzyloxycarbonyl azide, 1-benzylimidazole, benzyl-4-oxo-1-piperidinecarboxylate, fluorenylmethoxycarbonyl-4-piperidone, N-(benzyloxycarbonyl)glycinamide, N-(benzyloxycarbonyl)-1-H-pyrazole-1-carboxamidine, N-(benzyloxycarbonyl)-2-aminoacetonitrile.

19. A process for printing a time/temperature indicator according to claim 1, in which the bar code is printed by an inkjet printer.

20. A substrate on which is provided:
a bar code comprising a plurality of bars separated by spaces in a contrasting color, wherein at least some of the bars or the spaces are colored by a dye which will change color in the presence of a base to reduce the contrast between the bars and the spaces,
and
a neutral compound which, on exposure to energizing radiation, forms a base to initiate a color change in the dye.

21. The substrate of claim 20, wherein the neutral compound is a photolatent base.

22. A substrate on which is provided:
a bar code comprising a plurality of bars separated by spaces in a contrasting color, wherein at least some of the bars or the spaces are colored by a dye which will change color in the presence of an acid or a base to reduce the contrast between the bars and the spaces,
and
a neutral compound which, on exposure to energizing radiation, forms an acid or a base to initiate a color change in the dye,
wherein the dye is a leuco dye in its reduced form and the neutral compound is a thioxanthonium salt cationic photoinitiator.

23. A substrate according to claim 22, in which the cationic photoinitiator is a compound of formula:

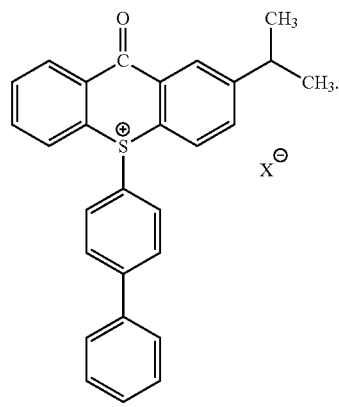

24. A substrate according to claim 22, in which the cationic photoinitiator is a compound of formula:

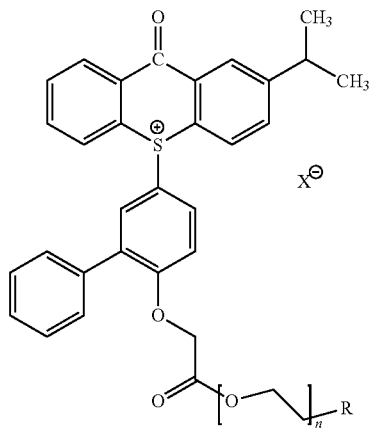

in which n is a number and R is a terminal group.

* * * * *